United States Patent [19]
Triplett et al.

[11] Patent Number: 5,453,370
[45] Date of Patent: Sep. 26, 1995

[54] METHOD FOR THE PREPARATION OF A PHOSPHOLIPID-DEPENDENT PROTHROMBIN ACTIVATOR FROM THE VENOM OF SNAKES

[75] Inventors: Douglas A. Triplett, South Muncie, Ind.; Kurt Stocker, Aesch, Switzerland

[73] Assignee: Pentapharm AG, Basel, Switzerland

[21] Appl. No.: 983,341

[22] Filed: Nov. 30, 1992

[30] Foreign Application Priority Data

Sep. 4, 1992 [EP] European Pat. Off. ............. 92810679

[51] Int. Cl.$^6$ ............................. C12N 9/50; C12N 9/48
[52] U.S. Cl. .......................... 435/214; 435/212; 424/542
[58] Field of Search .................................. 424/529, 542; 435/212, 219

[56] References Cited

U.S. PATENT DOCUMENTS

| | | | |
|---|---|---|---|
| 4,106,992 | 8/1978 | Vairel et al. | 195/66 B |
| 4,137,127 | 1/1979 | Stocker | 195/66 B |
| 4,610,879 | 9/1986 | Markland, Jr. et al. | 424/94 |
| 4,725,673 | 2/1988 | Herring | 530/381 |
| 5,112,949 | 5/1992 | Vukovich | 530/380 |
| 5,192,689 | 3/1993 | Hemker et al. | 435/13 |
| 5,219,995 | 6/1993 | Herring et al. | 530/381 |
| 5,260,060 | 11/1993 | Markland, Jr. et al. | 424/94.67 |

OTHER PUBLICATIONS

Owen, W. G. et al., "Trombosis Research". vol. 3(6), 1973, pp. 705–714.
Pirkle, H. et al, "Thrombosis Research," vol. 1(6), 1972, pp. 559–568.
Govers–Rienslag, J. W. P. et al., "Haenostasis and Animal Verams," *Hematology*, vol. 7, 1988., pp. 41–53. editor—H. Pirkle et al., Marcel–Dekker, Inc., New York, N.Y.
Speijer, H. et al, "Thrombosis and Haemostesis" vol. 57(3), 1987 (Jun.), pp. 349–355.
Owen, W. G., et al., "Thromb. Haemostasis," vol. 42(1), 1979 Jul., p. 400, #0954–abstract.
Whitaker, A. N. et al., "Aust N. Z. J. Med.," vol. 18(3, suppl. #2), 1988, p. 430, abstract.
Chester, A., et al., "Toxicon," vol. 20(2), 1982, pp. 501–504.
Lalloo, D., et al., "Toxicon," vol. 30(5–6), 1992, p. 528.
Speijer, H., et al., "The J. of Biological Chem.," vol. 261(28), Oct. 5, 1986, pp. 13258–13267.
Masci, P. P., et al., "Thrombosis Research," vol. 59, 1990, pp. 859–870.
Scopes, R. K., *Protein Purification—Principles and Practice*, 2nd ed., Springer–Volag, 1988, pp. 1, 17–20, 41–42, 50–54.
Deutscher, M. P., ed., *Methods in Enzymology*, vol. 182–Guide to Protein Purification, Academic Press, Inc., 1990, pp. 285, 292–295.
Fohlman, J., "Toxicon," vol. 17, 1979, pp. 170–172.
Tibballs, J., "Anaesth. Inters. Care," vol. 20(1), Feb. 1992, pp. 28–32.
Walker, F. J., et al., "Biochemistry," vol. 19, 1980, pp. 1020–1023.
Nakagaki, T., et al., "Thrombosis Research," vol. 65, 1992, pp. 105–116.
D. A. Triplett et al., "Lupus Anticoagulants: Misnomer, Paradox, Riddle Epiphenomenon," Hematol. pathol. 2, 121–143, 1988.
P. E. Love et al., "Antiphospholipid Antibodies: Anticardiolipin and the Lupus Anticoagulant in Systemic Lupus Erythematosus (SLE) and in Non–SLE Disorders," Ann. Int. Med. 112, 682–698, 1990.
T. Exner et al., SSC Subcommittee for the Standardization of Lupus Anticoagulants, "Guidelines for Testing and Revised Criteria for Lupus Anticoagulants," Thromb. Haemost. 65, 320–322, 1991.
J. Rosing et al., "Inventory of Exogenous Prothrombin Activators," Thrombosis and Haemostasis 65, 627–630, 1991.
P. P. Masci et al., "Purification and Characterization of a Prothrombin Activator from the Venom of the Australian Brown Snake, *Pseudonaja Textilis Textilis*," Biochemistry International, 17, 825–835, 1988.
C. Y. Lee (ed.), Snake Venoms, pp. 15–40, Springer Verlag, Berlin, Heidelberg, New York (1979).
H. Hofmann et al., "Blood Coagulation Induced by the Venom of *Bothrops atrox*. 1. Identification, Purification, and Properties of a Prothrombin Activator," Biochemistry, 26, 772–780 (1987).
T. Morita et al., "Purification and Properties of Prothrombin Activator from the Venom of *Echis carinatus*", J. Biochem. 83, 559–570 (1978).

*Primary Examiner*—Marian C. Knode
*Assistant Examiner*—K. Larson
*Attorney, Agent, or Firm*—Pennie & Edmonds

[57] ABSTRACT

A method for the preparation of a phospholipid-dependent prothrombin activator from the venom of snakes belonging to the Elapidae family, the activator comprising an increased plasma clotting activity in the presence of phospholipids and calcium ions; a reduced activity in the presence of Lupus Anticoagulant; an ability to facilitate clotting in a normal clotting time in the presence of platelet poor plasma, the plasma having normal or decreased levels of factor V, VII, VIII, IX, or X; and a major band with a molecular weight of 40,000 to 60,000 daltons on an SDS gel.

5 Claims, No Drawings

METHOD FOR THE PREPARATION OF A PHOSPHOLIPID-DEPENDENT PROTHROMBIN ACTIVATOR FROM THE VENOM OF SNAKES

FIELD OF THE INVENTION

The present invention relates to a phospholipid dependent prothrombin activator, to a method for its purification, and to a test for the detection of Lupus Anticoagulant using the activator.

BACKGROUND OF THE INVENTION

The lupus anticoagulant (LA) is an immunoglobulin (IgG, IgM, or a mixture of both) which interferes with one or more of the in vitro phospholipid dependent tests of coagulation (activated partial thromboplastin time [APTT]; prothrombin time [PT]; dilute Russell Viper Venom Time [dRVVT]). In contrast to specific inhibitors of coagulation proteins, LA has no reactivity with any of the individual coagulation factors. The name is a misnomer since the vast majority of patients do not have underlying systemic lupus erythematosus (SLE). More commonly, LA is secondary to infections, drugs (e.g. chlorpromazine, quinidine, procainamide) or it may be seen in an autoimmune disease which has recently been described: Primary Antiphospholipid Antibody Syndrome.

Paradoxically, LA is not associated with clinical bleeding unless there is some associated hemostatic defect (e.g. thrombocytopenia). Approximately 30 to 40% of patients with LA have a history of venous and arterial thromboembolic events. For a number of years, there has been much discussion as to whether LA was causative, a consequence, or coincident with thrombosis. More recent work in animal models would suggest that indeed LA is a cause of a thrombotic predisposition. Other clinical manifestations of LA include recurrent fetal loss, intrauterine fetal growth retardation, and prematurity. Also, LA may be associated with thrombocytopenia or autoimmune hemolytic anemias. Two recent excellent reviews discuss LA and its closely related antibody: anticardiolipin antibodies [Triplett D. A., Brandt J. T., Lupus Anticoagulants: Misnomer, Paradox, Riddle Epiphenomenon. Hematol. Pathol. 2, 121–143, 1988; Love P. E., Santoro S. A., Antiphospholipid Antibodies: Anticardiolipin and the Lupus Anticoagulant in Systemic Lupus Erythematosus (SLE) and in Non-SLE Disorders. Ann. Int. Med. 112, 682–698, 1990].

In most cases, LA is detected serendipitous as a result of an unexplained prolonged APTT and/or PT. Typically, an abnormal APTT is associated with quantitative or qualitative deficiencies in factors XII, XI, IX, VIII, V, or X while PT prolongation generally indicates a deficiency in either factor II, V, VII, X, or fibrinogen. Mixing patient plasma with a source of normal platelet poor plasma will result in lack of correction of the prolonged APTT and/or PT. Lack of correction is a sine qua non for the diagnosis of an inhibitor (synonym circulating anticoagulant).

The diagnosis of LA is often difficult. Commercially available APTT reagents show a wide range of sensitivity to LA and there appears to be differences between IgG and IgM LA. In addition to the APTT, other tests have been used to screen for LA including: dilute Russell Viper Venom Time (dRVVT), Kaolin Clotting Time, and dilute APTT. The performance of these tests is difficult requiring mixing patient and normal plasma in the case of the Kaolin Clotting Time and dilute APTT. Consequently, these tests are not readily automated with conventional coagulation instrumentation. Furthermore, if commercial freeze-dried plasmas are used as a source of normal plasma for the mixing studies, there may be false negative results due to a high content of phospholipids in the lyophilized commercial preparations.

Once a patient plasma has been established as having a prolonged screening study with lack of correction by mixing with normal platelet poor plasma, it is necessary to confirm the phospholipid specificity of the inhibitor. Two contrasting approaches have been utilized. The first of these employs a dilute phospholipid test system (e.g. tissue thromboplastin inhibition [TTI]) to accentuate the inhibitor effect. The second approach utilizes a source of excess phospholipids (e.g. Platelet Neutralization Procedure [PNP]) to "bypass" or "neutralize" the LA. Comparative analysis of these two different approaches suggests the PNP is more sensitive than the TTI.

In addition to the heterogeneity of commercial available reagents, patient plasmas demonstrate remarkable heterogeneity suggesting that there is a family of antibodies with LA activity. The problems of diagnosing LA have been highlighted by the deliberations of the SSC Subcommittee for Standardization of Lupus Anticoagulants (Exner, T. et al., SSC Subcommittee for the Standardization of Lupus Anticoagulants, Guidelines for Testing and Revised Criteria for Lupus Anticoagulants. Thromb. Haemost. 65, 320–322, 1991).

The venoms of several snake species contain enzymes that convert the zymogen prothrombin into the enzyme thrombin and/or its catalytically active precursor meizothrombin. Both activation products convert fibrinogen into fibrin and thereby cause plasma coagulation. Also, both thrombin and meizothrombin catalyze the hydrolyric release of chromophore from synthetic chromogenic thrombin sensitive substrates. Some of these snake venom prothrombin activators do not require a cofactor while a second group depends on the presence of calcium ions and phospholipid. A third group needs factor V in addition to calcium and phospholipid. A review on snake venom prothrombin activators is presented by: Rosing J., Tans G., Thromb. Haemost. 65, 627–630, 1991.

Phospholipid dependent prothrombin activators whose potency is enhanced by phospholipid but not by factor V have been found in the venom of snakes belonging to the Elapidae family, especially members of the Oxyuranus and Pseudonaja genera. A method for the purification of the prothrombin activator from the venom of Pseudonaja textilis using chromatography on cancanavalin A-sepharose and gel filtration is described by Masci P. P. et al., Biochemistry International 17, 825, 1988. A commercial preparation of the activator prepared according to this method is available from Venom Supplies, Tanunda, Australia. The prothrombin activator isolated from P. textills venom according to Masci et al. is a protein with a molecular mass of greater than 200,000 daltons consisting of several non-covalently linked subunits as shown by polyacrylamide gel electrophoresis in the presence of sodium dodecylsulfate (SDS-PAGE). The activator according to Masci et al. (1988) was able to clot citrated plasma in the absence of calcium ions. Its plasma clotting activity was, however, stimulated 2.5 fold in the presence of calcium but no additional stimulation was observed with the addition of phospholipids.

Prothrombin activators which are insensitive to phospholipids can be isolated from venoms of snakes belonging to the family Viperidae, especially from venoms of species belonging to the genera Echis, Tryncresurus and Bothrops using conventional protein separation techniques as described by R. K. Scopes, Protein Purification, Springer-Verlag, New York, Heidelberg, Berlin, 2nd edition, (1987). A review on the zoological classification of venomous snakes can be found in G. Underwood, Classification and distribution of venomous snakes in the world. In: C. Y. Lee (ed). Snake Venoms p. 15–40, Springer Verlag: Berlin, Heidelberg, New York (1979). A specific method for the isolation of the prothrombin activator from *Bothrops atrox* venom is described by Hofmann H. and Bon C., Biochemistry 26, 772 (1987) and the method for the preparation of ECARIN (phospholipid independent protrombin activator derived from Echis Carinatua venom) from *Echis carinatus* venom is provided by Morita T. and Iwanaga S., J. Biochem. 83, 559 (1978). ECARIN activator is commercially available from Pentapharm Ltd., Basle, CH. One ecarin unit is the amount of ECARIN activator which under defined conditions generates one International Unit (U) of enzyme activity from prothrombin as measured with the synthetic chromogenic thrombin substrate Tos-Gly-Pro-Arg-pNA (1 U being the amount of enzyme which hydrolyzes 1 µM of substrate per minute under standard conditions).

SUMMARY OF THE INVENTION

It was found that the clotting time of human citrated plasma following the addition of crude venom from the Australian brown snake *Pseudonaja textilis*, or of the commercially available prothrombin activator from this venom, was slightly shortened by the presence of phospholipid and calcium ions. It was also found that coagulation induced by *P. textilis* venom or by the commercial activator thereof (prepared according to Masci et al.), in the presence of phospholipid and calcium was not significantly delayed in LA containing plasma, as compared to normal plasma. It was then surprisingly found that the venom of *P. textilis* contained two different prothrombin activators, one of which required phospholipids and calcium ions for its action and was sensitive to LA, the second one acted independent from phospholipid and calcium and was insensitive to LA. It was moreover found that the phospholipid dependent prothrombin activator (PLDPA) from *P. textilis* venom was adsorbed to barium sulfate, while the phospholipid-independent prothrombin activator (PLIPA) remained in solution and that a simple purification process for the phospholipid-dependent activator could be based on this behaviour.

It was then found that PLDPA, purified by barium sulfate adsorption, exerted a very low plasma clotting activity in the absence of calcium and that the plasma clotting time measured following the addition of PLDPA in the presence of phospholipid and calcium was strongly prolonged by the presence of LA. It was in addition found that the clotting time, measured following the addition of the ECARIN activator was equal in both normal and LA containing plasma and it was finally found that both PLIPA and PLDPA clotting tests gave normal results with plasma depleted in factor V, VIII or X, respectively.

It is an object of the invention to provide a PLDPA from snake venom which can be used for the determination of LA.

It is another object of the invention to provide a method of purification of the snake venom.

It is still another object of the invention to provide different tests for the determination of LA and test kits which can be used for it.

DESCRIPTION OF THE PREFERRED EMBODIMENTS

PLDPA, free from contaminating PLIPA, is obtainable from aqueous solutions of the crude venom of *Pseudonaja textills, P. affinis, P. nuchalis, Oxyuranus scutellatus* or *O. microlepidotus*, by 1.) adsorption to a practically water-insoluble barium salt e.g. barium sulfate, barium citrate, barium phosphate or by adsorption to aluminium hydroxide, magnesium hydroxide or tricalcium phosphate, 2.) washing the adsorbate with water or saline to remove non-adsorbed protein, 3.) elution of PLDPA with an aqueous solution of the alkali-, ammonium- or organic amine salt of acids which form practically insoluble salts, complexes or chelates with earth alkali- and aluminium ions e.g. citrate, morpholino ethane sulfonate, phosphate or ethylene diamine tetraacetate and 4.) removal of eluent by ultrafiltration, dialysis or gel filtration. The resulting PLDPA migrated by electrophoresis in the presence of SDS in a gel gradient of 8 to 25% polyacrylamide as one major band with a mobility corresponding to molecular mass of 40,000 to 60,000 Daltons and one or two minor bands with molecular mass between 100,000 and 150,000 Daltons. The plasma clotting activity measured on platelet poor human plasma of PLDPA according to the present invention was stimulated approximately 20 times by the addition of calcium ions and approx. 50 times by the addition of both calcium ions and phospholipid.

A clotting test, sensitive to LA can be carried out by mixing a plasma sample with a suitable amount of a phospholipid suspension and a solution of PLDPA, and by measuring the clotting time upon the addition of a sufficient amount of calcium chloride solution. The PLDPA clotting time is prolonged in LA containing plasma as compared to normal plasma; it is also prolonged in case of a quantitative or qualitative prothrombin abnormality, but it remains unaffected by deficiencies in factors V, VII, VIII, IX or X.

The clotting test can be simplified by the preparation of a reconstitutable reagent which contains PLDPA and phospholipid in a stable, co-lyophilized form. If desirable, the amount of calcium ions required for this test can also be co-lyophilized with PLDPA and phospholipid, if a non-hygroscopic calcium salt with a low freezing point depressor activity e.g. calcium gluconate or calcium lactobionate is used.

A chromogenic test for LA can be performed by mixing a plasma sample with PLDPA and phospholipid, adding calcium chloride, incubating this mixture for a defined activation time, quenching the prothrombin activation process by the addition of a chelating agent e.g. ethylene diamine tetraacetate containing buffer and measuring the generated amount of thrombin by means of a chromogenic substrate e.g. Tos-Gly-Pro-Arg-pNA. The amount of thrombin generated in LA containing plasma is significantly smaller as compared to the amount generated in normal plasma; it is also smaller in case of a qualitative or quantitative prothrombin abnormality.

A clotting test for LA, the result of which is not affected by a prothrombin deficiency, comprises the determination of the plasma clotting time after the addition of a PLIPA e.g. ECARIN, measurement of the clotting time after the addition of phospholipid and of a PLDPA, and calculation of the PLIPA/PLDPA clotting time ratio and/or the PLDPA/ PLIPA clotting time ratio. Both PLIPA and PLDPA clotting times are inversed proportional to the prothrombin content of the plasma sample. However, while LA present in the sample, by interaction with the added phospholipids, causes a prolongation of PLDPA clotting time, the ECARIN activator clotting time remains unaffected. A PLIPA/PLDPA clotting time ratio below 1 or a PLDPA/PLIPA clotting time ratio above 1 (within reference interval) therefore indicates the presence of LA or of prothrombin with a molecular abnormality. The potency of PLIPA and PLDPA reagents according to the present invention is with preference adjusted in such a way that both reagents clot normal human plasma under defined conditions within the same time e.g. 20 seconds. The reagents for the PLIPA- and PLDPA test can be prepared in a liquid form with a limited stability, to be used within a limited time period or can be manufactured as stable, freeze dried preparations to be reconstituted with water or buffer to obtain the ready-for-use solution.

An immunochromogenic principle for an LA test can be carried out by coating a microtiter plate with phospholipid, adding a series of normal and patient plasma samples into the wells (to bind LA to the phospholipid layer), removal of plasma by rinsing, addition of a PLDPA and calcium-containing prothrombin solution to each well, quenching the activation by the addition of a chelating agent, adding a synthetic chromogenic thrombin substrate, quenching the reaction with acetic acid after a defined incubation period and measuring released chromophore by means of a microtiter plate reading photometer. This test principle is not affected by prothrombin abnormalities.

By the incorporation of prothrombin as the substrate for PLDPA in any of the above test methods, an interference by qualitative and/or quantitative prothrombin abnormalities can be avoided.

Phospholipids suitable for the performance of the PLDPA tests are preparations containing phosphatidylethanolamine (Synonym: colamine kephalin) and phosphatidylserine (Synonym: serine kephalin) which are obtainable from animal, plant or microbial biomass by organic solvent extraction. Suitable phospholipid preparations e.g. from bovine brain, egg yolk or soy bean are commercially available from Sigma Chemical Company, St. Louis, Mo., USA.

A stable, PLDPA reagent for reconstitution is obtainable by dissolving PLDPA purified according to the present invention and a protein-stabilizing polymer e.g. a collagen derived polypeptide and/or bovine serum albumin and/or dextran in water or buffer, adding a phospholipid suspension and freeze-drying this mixture after subdivision into vials suitable for reconstitution. If desirable, a lyophilizable calcium salt e.g. calcium gluconate or calcium lactobionate can be added.

A stable, PLIPA reagent for the PLIPA test according to the present invention is obtainable by dissolving ECARIN activator and a stabilizing polymer e.g. serum albumin and/or a collagen derived polypeptide and/or dextran in water or in a buffer solution and freeze-drying this solution subdivided into vials suitable for reconstitution.

The pH of the test reagents is adjusted to 7 to 8 preferentially to 7.4 and stabilized by means of a buffer system. Suitable buffer systems comprise for example tris-(hydroxymethyl)-aminomethane hydrochloride (TRIS-HCl), 2-(N-morpholino)ethane-sulfonic acid (MES) and N-2-hydroxy-ethylpiperazine-N'-ethane-sulfonic acid (HEPES).

The PLIPA and PLDPA tests for LA in plasma can be carried out by measuring the time until onset of fibrin formation in the reaction mixture by manual or mechanical detection of gel formation or by photometric turbidity measurement.

EXAMPLE 1

Preparation of PLDPA from P. textilis venom 50 mg crude P. textilis venom was dissolved in 100 ml aqueous tri-sodium citrate solution. 8 ml barium chloride solution, 1 M, were added, the mixture was stirred for 30 minutes, the formed precipitate was separated by centrifugation and dissolved in 33 ml of an aqueous solution of citrated saline (sodium chloride, 0.15 M and tri-sodium citrate 0.02 M). 2.64 ml of barium chloride, 1 M, were added to the solution and after 30 min. stirring, the formed precipitate was separated by centrifugation and the sediment was washed with 33 ml citrated saline. The washed sediment was dissolved in EDTA 0.2 M, pH 7.4, and EDTA-barium chelate was removed by ultrafiltration through a membrane with a cut-off of 10,000 Daltons and extensive washing with saline. The retentate was lyophilized to yield PLDPA which migrated in SDS-PAGE, using a gradient of 8 to 25% polyacrylamide, as one major band at a mobility corresponding to a molecular mass of 53,000 Daltons and two minor bands showing a molecular mass of 110,000 to 130,000 Daltons, respectively. A PLDPA solution adjusted to clot normal human citrated plasma in the presence of calcium chloride, 12.5 mM, and rabbit brain phospholipid, 17 μg/ml, within 20 seconds, showed a plasma clotting time in the absence of calcium ions and phospholipid of >900 seconds.

EXAMPLE 2

Preparation of a Textarin reagent for testing phospholipid-dependent prothrombin activation TEXTARIN activator prepared according to example 1 was dissolved in a solvent mixture consisting of 1% collagen-derived polypeptides (Prionex™, Pentapharm) in 0.05 molar HEPES buffer pH 7.4, to make 50 ml of stock solution I. TEXTARIN is Pentapharm AG's trademark for the prothrombin activating component of Pseudonaja Textilis snake venom used to the Lupus Anticoagulant test of this invention. It is referred to generically herein as "PLDPA". PRIONEX is a polypeptide fraction for the stabilization of proteins.

500 mg rabbit brain kephalin were homogenized in 5000 ml solvent mixture to obtain stock solution II.

Serial dilutions of stock solution I were prepared by mixing with stock solution II. The clotting time of citrated normal human plasma was then measured with each dilution using the following procedure: 0.1 ml dilution and 0.1 ml calcium chloride solution 0.025 M were incubated for 3 minutes at 37° C., 0.1 ml normal human plasma was then added and the clotting time was measured manually. A mixture of 1 volume stock solution I and 64 volumes stock solution II clotted normal plasma within 20 seconds. The total amount of PLDPA stock solution was diluted and mixed with kephalin accordingly, subdivided into 1.0 ml portions, filled into siliconized vials and freeze dried. The freeze-dried product, upon reconstitution with distilled water (1 ml per vial), gave a reagent which clotted citrated normal human plasma within 20±2 seconds in a test mixture composed of 0.1 ml plasma, 0.1 ml Textarin reagent and 0.1 ml CaCl$_2$.

EXAMPLE 3

Preparation of ECARIN activator reagent for testing phospholipid-independent prothrombin activation 10 mg ECARIN activator with a potency of 500 EU per mg (ECARIN activator is a Pentapharm AG trademark for prothrombin activator derived from Echis Carinatus venom) were dissolved in 50 ml of a solvent mixture consisting of 1% collagen-derived polypeptides (Prionex™, Pentapharm) in 0.05 molar HEPES buffer pH 7.4, to obtain ECARIN activator stock solution. Serial dilutions of stock solution with solvent mixture were prepared and the clotting time of citrated normal human plasma was measured manually at 37° C. using a test mixture of 0.2 ml plasma and 0.1 ml ECARIN activator dilution. The dilution which clotted normal plasma within 20 seconds was determined and the ECARIN activator stock solution was diluted accordingly to yield a solution with approx. 16 EU per ml, ready for freeze-drying. The solution was subdivided into portions of 1.0 ml, filled into suitable vials and freeze-dried. The freeze-dried product, after reconstitution with 1.0 ml distilled water, gave a reagent which clotted citrated normal human plasma in 20±2 seconds, in a test mixture composed of 0.2 ml plasma and 0.1 ml ECARIN activator reagent.

EXAMPLE 4

TEXTARIN activator and ECARIN activator clotting test for LA

TEXTARIN activator reagent according to example 2 and ECARIN activator reagent according to example 3 were reconstituted with 1.0 ml distilled water per vial.

TEXTARIN activator and ECARIN activator clotting times of plasma samples collected from ten pre-operative patients with a normal blood coagulation status and of ten plasma samples containing LA, as verified immunologically, were determined. The results are listed in tables 1 and 2.

TABLE 1

Ecarin activator and Textarin activator clotting times of plasma with a normal clotting status

| Plasma | Ecarin activator ct (sec.) | Textarin activator ct (sec.) | Textarin/Ecarin activators ratio |
|---|---|---|---|
| 1 | 17.3 | 21.2 | 1.23 |
| 2 | 18.7 | 18.0 | 0.96 |
| 3 | 20.2 | 19.5 | 0.97 |
| 4 | 17.1 | 18.1 | 1.06 |
| 5 | 17.1 | 17.9 | 1.05 |
| 6 | 17.0 | 17.6 | 1.04 |
| 7 | 17.4 | 18.6 | 1.07 |
| 8 | 14.6 | 17.9 | 1.23 |
| 9 | 15.8 | 17.4 | 1.10 |
| 10 | 20.6 | 17.5 | 0.85 |

TABLE 2

Ecarin activator and Textarin activator clotting times of LA-containing plasma

| Plasma | Ecarin activator ct (sec.) | Textarin activator ct (sec.) | Tex./Ec. ratio |
|---|---|---|---|
| 11 | 17.4 | 27.8 | 1.60 |
| 12 | 13.9 | 34.1 | 2.45 |
| 13 | 19.0 | 24.7 | 1.30 |
| 14 | 14.4 | 40.7 | 2.83 |
| 15 | 16.6 | 38.8 | 2.34 |
| 16 | 18.7 | 41.2 | 2.20 |
| 17 | 20.5 | 75.5 | 3.68 |
| 18 | 21.1 | 90.1 | 4.27 |
| 19 | 14.4 | 28.2 | 1.96 |
| 20 | 15.9 | 58.9 | 3.70 |
| 21 | 22.5 | 38.8 | 1.72 |
| 22 | 17.8 | 75.9 | 4.26 |

EXAMPLE 5

Chromogenic TEXTARIN activator test

Material: TEXTARIN activator reagent according to example 2 was reconstituted with 1 ml distilled water per vial. The chromogenic thrombin substrate Tos-Gly-Pro-Arg-pNA (CHROMOZYM activator $TH^R$, a tripeptide for the determination of proteolytical enzymes manufactured by Pentapharm Ltd., distributed by Boehringer-Mannheim) was dissolved in distilled water at a concentration of 4 μmoles per ml. Calcium chloride/GPRP solution contained 0.025 mmoles $CaCl_2$ and 0.5 mg Gly-Pro-Arg-Pro (GPRP, Pefabloc $FG^R$, an inhibitor of fibrin polymerisation, Pentapharm) per ml. EDTA-buffer was glycine-NaOH buffer, 0.3 M, pH 8.4, 0.75 mM in $EDTA.Na_2$. Test: 0.020 ml TEXTARIN activator reagent and 0.020 ml $CaCl_2$/GPRP were pipetted into a photometric cuvette and preheated for 2 minutes at 37° C., 0,020 ml plasma sample were added and incubated for exactly 30 seconds at 37° C. The activation process was quenched by the addition of 1.74 ml EDTA-buffer, 0.200 ml Chromozym $TH^R$ were added and the p-nitroaniline release catalyzed by generated thrombin was recorded with a photometer at a wave length of 405 nm. The difference in absorbance per minute (DA 405/min.) which is directly proportional to the generated amount of thrombin was measured in normal and LA containing plasma samples.

Results: DA 405/min. values of normal plasma varied between 0.07 and 0.1, whereas LA containing plasma samples gave values of 0.02 to 0.06.

EXAMPLE 6

Preparation of phospholipid dependent prothrombin activator (PLDPA) from venom of different snake species Samples of 5 mg each of dried, crude venom from Oxyuranus scutellatus, O. microlepidotus, Pseudonasa textills, P. inframaculata and P. nuchalis were dissolved in 10 ml aqueous tri-sodium citrate solution. 0.8 ml barium chloride solution, 1 M, was added, the mixture was stirred for 30 minutes, the formed precipitate was separated by centrifugation and dissolved in 3 ml of an aqueous solution of citrated saline (sodium chloride, 0.15 M and tri-sodium citrate 0.02 M). 0.25 ml of barium chloride, 1 M, was added to the solution and after 30 min. stirring, the formed precipitate was separated by centrifugation and the sediment was dissolved in EDTA 0.2 M, pH 7.4 to obtain a stock solution for prothrombin activation tests.

Human plasma clotting time was measured with dilutions of each stock solution in the presence and absence of phospholipid and calcium ions. The results are presented in table 3.

TABLE 3

Clotting time of PLDPA from different snake venoms

| | | clotting time (sec) | |
|---|---|---|---|
| Species | dilution of stock soln. | Ca/PL present | Ca/PL absent |
| | | (double determination) | |
| O. scutellatus | 1/200 | 41.2/41.2 | 111.0/112.0 |
| O. microlepidotus | 1/200 | 34.0/34.0 | 151.0/151.0 |
| P. textilis | 1/1000 | 26.0/27.0 | 230.0/233.0 |
| P. inframaculata | 1/500 | 25.0/25.0 | 112.0/114.0 |
| P. nuchalis | 1/500 | 30.0/30.0 | 75.0/74.0 |

We claim:

1. A method for the preparation of a phospholipid-dependent prothrombin activator from the venom of snakes belonging to Elapidae family, said activator has an increased plasma clotting activity in the presence of phospholipids and calcium ions; a reduced activity in the presence of Lupus Anticoagulant; an ability to facilitate clotting in a normal clotting time in the presence of platelet poor plasma, said plasma having normal or decreased levels of factor V, VII, VIII, IX, or X, and a major band with a molecular weight of 40,000 to 60,000 Daltons on an SDS gel, said method comprising:

a) adsorbing the venom on a water-insoluble barium, magnesium, calcium or aluminum salt, b) eluting the activator from the venom with an aqueous solution of alkali-, ammonium- or organic amine salts to form insoluble salts, complexes or chelates with alkaline earth or aluminum ions, c) removing the eluted salts, and d) recovering the activator.

2. The method according to claim 1, wherein the venom is absorbed on barium citrate, barium phosphate, aluminium hydroxide, magnesium hydroxide, tricalcium phosphate, or barium sulfate.

3. The method according to claim 1, wherein the activator is eluted with an aqueous solution of a citrate, morpholino ethane sulfonate, phosphate or ethylene diamine tetraacetate salt.

4. The method according to claim 1, wherein the eluted salts are removed by ultrafiltration, dialysis or gel filtration.

5. The method according to claim 2 wherein the venom is absorped on barium sulfate.

* * * * *